Feb. 19, 1957 C. LORETTO ET AL Plant Pat. 1,567
RASPBERRY PLANT
Filed March 7, 1956
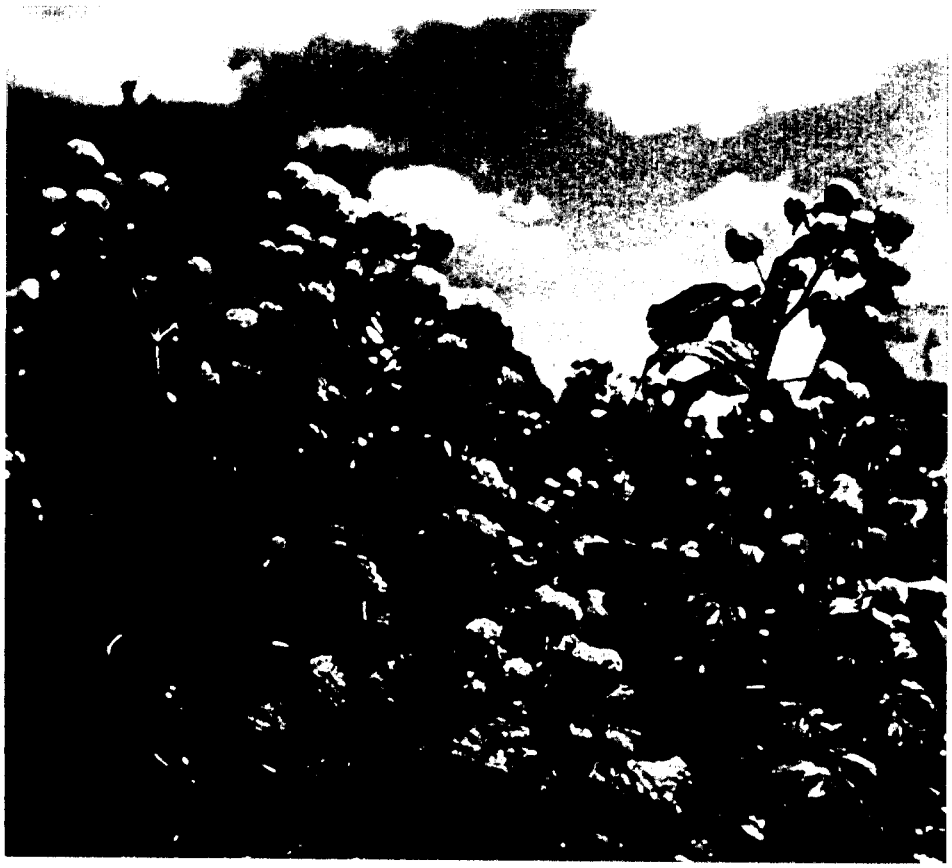
INVENTORS
Conio Loretto,
Joseph Loretto &
Leonard Loretto,
BY Beau, Brooks, Buckley + Beau.
ATTORNEYS.

United States Patent Office

Plant Pat. 1,567
Patented Feb. 19, 1957

1,567

RASPBERRY PLANT

Conio Loretto, Joseph N. Loretto, and Leonard Loretto, Brant Township, Erie County, N. Y., assignors to First Burgundy, Inc., Brant Township, Erie County, N. Y., a corporation of New York Application March 7, 1956, Serial No. 570,198

1 Claim. (Cl. 47—62)

The present invention relates to a new and distinct variety of raspberry plant.

The fruit of this new variety is of very good flavor, being sweet and sub-acid, and of excellent eating quality, and characterized particularly by its very attractive burgundy color.

The enclosed drawing and the specification to follow present the distinctions in characteristics of the variety of plant of the present invention, which plant has been asexually reproduced.

The accompanying drawing shows specimen plants as grown by us in the township of Brant, county of Erie, in the State of New York.

The plant of our invention grew as a sport on a Plum Farmer Black Raspberry bush (unpatented) growing in proximity to Webster Purple Raspberry bushes (unpatented). We then produced other plants from this sport by tipping or inarching the same. The original sport and the subsequent plantings both occurred on land leased and cultivated by the applicants from a time long prior to the occurrences described above and since purchased by applicants, such land being located on the Versailles Plank Road in the township of Brant, county of Erie, and State of New York.

The plants of our invention have been asexually reproduced by us in the State of New York, in the township of Brant in the manner common to asexually reproducing varieties of black and purple raspberry plants, that is by tipping or inarching branches therefrom.

At maturity the plants are large, growing to a height of twelve to fifteen feet if unpruned, and the plants are vigorous, erect, dense and very productive. The plants grown and described herein exhibit the qualities and characteristics set forth in this specification as grown in the sunny and cool climate prevailing in Western New York, conditions being moderately moist.

The following is a detailed description of our new variety of raspberry plant grown as described above.

Stem: Canes relatively heavy, erect, very tall; prickly, but otherwise essentially glabrous, rooting at tip. Prickles: Few, averaging about 7 in a cylinder of cane surface one inch in length; nearly erect, very slightly retrorse; mostly 2.5 to 3.0 mm. in length, stouter toward the oval base which measures 1.3 to 2.0 mm. in length in older parts of cane.

Leaves: Leaves of young primocanes mostly pinnate, with 3 to 5 ovate to lanceolate, acute, serrate to double serrate leaflets, the basal pair of leaflets with a stalk 1 mm. or less in length, the upper pair sessile, the terminal leaflet in a 5-divided leaf with a stalk 2 to 3 mm. in length; upper side sparsely puberulous or glabrous, lower side tomentose, especially on veins; petiole and rachis puberulous-tomentose, with scattered pinkish bristles or prickles, of which one or two are found on the midrib of the leaflets, near its base; upper side of the rachis slightly grooved; stipules persistent adherent to the petioles for ¼ to ½ the total length of the stipule, varying from 8 to 18 mm. in total length in a young plant having about 10 internodes. Leaves of floricanes apparently essentially similar.

Bloom: 5 to 15 flowers in an irregular cyme which is essentially erect or leaning, but not drooping; the inflorescence includes subordinate cymes or corymbs borne in the axils of the uppermost bracts or leaves.

*a.* Pedicels: 5 to 40 mm. in length, bearing prickles.
*b.* Peduncles: bearing few prickles, which are essentially like those of the cane.
*c.* Calyx 5-parted, its lobes 4 to 7 mm. in length, tomentose on under side, their tips acute (boat-shaped in dried specimens examined).
*d.* Petals large, white.
*e.* Date of earliest flowering: May 30–31st.
*f.* Length of flowering season: two weeks.

Fruit:

*a.* Color: Burgundy (Color Plate 56E–8 in Maerz & Paul's "Dictionary of Color") with a paler pink reticulum on the surface which is visible with magnification.
*b.* Drupelets: mostly from 50 to 80 in the aggregate fruit, averaging about 63, measuring about 3.0 to 4.5 x 4.5 to 5.5 mm., the pulp firm and meaty. Pyrenes elongate-reniform, 1.4 to 2 x 2.5 to 3.5 mm.
*c.* Style: often persistent, pinkish, about 3 mm. in length.
*d.* Torus: conical and truncate, with the upper part more nearly cylindrical than the basal part, the difference between these two parts being relatively abrupt and conspicuous on the exposed torus.
*e.* Keeping quality: excellent; fruit holds shape after picking.
*f.* Shipping quality: good.
*g.* Picking quality and adherence: detaches easily when ripe but does not fall off the torus; the erect, non-dropping habit of the floricanes makes picking the fruit much easier than with most varieties, and keeps the fruit cleaner and freer of soil brought by splashing of rain.
*h.* Flavor: sweet, sub-acid.
*i.* Aroma: distinct and pleasant, pervading the entire field where they are grown.
*j.* Eating quality: very good to excellent.
*k.* Picking season: first picking July 3 to 5. Last picking July 15 to 20. Length of picking season: 2 weeks.

Under field conditions at North Collins in the township of Brant, county of Erie, State of New York, the productivity of the variety of raspberry plant of the present invention is much greater than that of any variety known to the inventors.

We claim:

A new and distinct variety of raspberry plant, substantially as herein shown and described, characterized particularly as to novelty by the burgundy color of its fruit, and further characterized by its vigorous, erect and dense growth and high productivity.

No references cited.